United States Patent [19]

Allphin

[11] Patent Number: 5,166,352
[45] Date of Patent: Nov. 24, 1992

[54] PYRIDINECARBOXYLIC ACID CHLORIDES FROM (TRICHLOROMETHYL)PYRIDINES

[75] Inventor: Clark P. Allphin, Concord, Calif.

[73] Assignee: DowElanco, Indianapolis, Ind.

[21] Appl. No.: 758,012

[22] Filed: Sep. 12, 1991

[51] Int. Cl.$^5$ ............... C07D 213/55; C07D 213/54; C07D 213/26

[52] U.S. Cl. .................................. 546/314; 546/315; 546/316; 546/318; 546/323; 546/327

[58] Field of Search ............... 546/314, 315, 316, 323, 546/327, 318

[56] References Cited

U.S. PATENT DOCUMENTS 3,317,549  5/1967  Johnston .
4,587,116  5/1986  Livingston et al. .

Primary Examiner—C. Warren Ivy
Assistant Examiner—Barbara Twardzik
Attorney, Agent, or Firm—D. Wendell Osborne

[57] ABSTRACT

Pyridinecarboxylic acids and their acid chloride, aliphatic ester and alkylamide derivatives are prepared by passing vapors of a (trichloromethyl)pyridine compound, such as 2,3-dichloro-5-(trichloromethyl)pyridine over gamma-alumina at a temperature of about 250° C. to 450° C. to obtain a pyridinecarboxylic acid chloride compound, such as 2,3-dichloronicotinoyl chloride and, if desired, subsequently converting this compound to its acid, an ester, or an amide, such as 2,3-dichloronicotinic acid, methyl 2,3-dichloronicotinate, or N-methyl-2,3-dichloronicotinamide, by treatment with water, an aliphatic alcohol, or ammonia or an alkylamine, respectively.

7 Claims, No Drawings

PYRIDINECARBOXYLIC ACID CHLORIDES FROM (TRICHLOROMETHYL)PYRIDINES

BACKGROUND OF THE INVENTION

The present invention relates to a process for the preparation of optionally substituted pyridinecarboxylic acid chlorides (picolinoyl, nicotinoyl, and isonicotinoyl chlorides) by hydrolysis of optionally substituted (trichloromethyl)pyridine compounds. The acid chlorides prepared can serve as intermediates in the preparation of optionally substituted pyridinecarboxylic acids, esters, and amides.

Pyridinecarboxylic acids and many substituted pyridinecarboxylic acids are known and are known to be preparable by the hydrolysis of the corresponding (trichloromethyl)pyridine compound in a strong acid, such as sulfuric acid or nitric acid (U.S. Pat. No. 3,317,549). It is also known that related strong acid hydrolyses can be stopped at the acid chloride stage. Carboxylic acid chlorides are typically prepared from the corresponding acids by treatment with an inorganic acid chloride, such as thionyl chloride or phosphoryl chloride. Each of these processes produces large amounts of waste products. Processes for converting (trichloromethyl)pyridine compounds to pyridinecarboxylic acid chloride compounds that are simpler and do not create such by-products would be of considerable value in the preparation of pyridinecarboxylic acid chlorides and many commercially significant pyridinecarboxylic acid, ester, and amide compounds.

It is known that chloro(trichloromethyl)pyridine compounds react with aluminum oxide at temperatures over 500° C. to produce aluminum chloride, nitrogen, carbon dioxide, and carbon monoxide (U.S. Pat. No. 4,587,116).

SUMMARY OF THE INVENTION

It has now been found that optionally substituted (trichloromethyl)pyridine compounds can be converted to optionally substituted pyridinecarboxylic acid chlorides by passing the (trichloromethyl)pyridine compounds in the vapor state over aluminum oxide. The optionally substituted pyridinecarboxylic acid chloride compound obtained can be recovered or can be converted to the corresponding acid, an ester, or an amide by subsequent treatment with water, an alcohol, or ammonia or a primary or secondary amine, respectively.

The invention includes a process for the preparation of a pyridinecarboxylic acid chloride compound of Formula I:

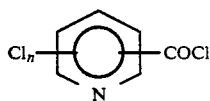

Formula I wherein
n represents an integer of 0 to 4
which comprises contacting a (trichloromethyl)pyridine compound of Formula 11:

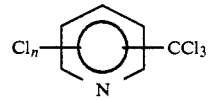

Formula II wherein
n represents an integer of 0 to 4
with aluminum oxide in the vapor phase at a temperature of about 250° C. to about 450° C.

The invention further embraces a process for the preparation of a pyridinecarboxylic acid or an ester or an amide derivative thereof of Formula III:

Formula III wherein
X represents OH, O($C_1$–$C_{12}$ alkyl), $NH_2$, NH($C_1$–$C_{12}$ alkyl), or N($C_1$–$C_{12}$ alkyl)$_2$; and
n represents an integer of 0 to 4
which comprises contacting a (trichloromethyl)pyridine compound of Formula II wherein n represents an integer of 0 to 4 with aluminum oxide in the vapor phase at a temperature of about 250° C. to about 450° C. to obtain a pyridinecarboxylic acid chloride compound of Formula I wherein n represents an integer of 0 to 4 and subsequently combining said acid chloride compound with water, an aliphatic alcohol having 1 to 12 carbon atoms, ammonia, or a primary or secondary alkylamine having 1 to 12 carbon atoms in each alkyl moiety.

DETAILED DESCRIPTION OF THE INVENTION

The compounds produced by the process of the present invention, compounds of Formulas I and 111 wherein n represents an integer of 0 to 4 and X represents OH, O($C_1$–$C_{12}$ alkyl), $NH_2$, NH($C_1$–$C_{12}$ alkyl), or N($C_1$–$C_{12}$ alkyl)$_2$, are optionally chlorinated pyridinecarboxylic acids and their acid chloride, aliphatic ester, and amide derivatives. Optionally chlorinated picolinic acids (pyridine-2-carboxylic acid compounds), nicotinic acids (pyridine-3-carboxylic acid compounds), and isonicotinic acids (pyridine-4-carboxylic acid compounds) and their acid function derivatives are included. Typical pyridinecarboxylic acids and their derivatives that can be produced are nicotinic acid, nicotinamide, methyl 6-chloronicotinate, butyl 2,6-dichloroisonicotinate, 2-chloro-N,N-diethylisonicotinamide, N-octyl-2,5,6-trichloronicotinamide, 3,6-dichloropicolinoyl chloride, 3,4,5,6-tetrachloropicolinic acid, 2,3,5,6-tetrachloroisonicotinoyl chloride, 1-methylheptyl 6-chloropicolinate, and 5,6-dichloronicotinoyl chloride.

The starting materials for the present process are optionally chlorinated (trichloromethyl)pyridines of Formula II wherein n represents an integer of 0 to 4. Suitable (trichloromethyl)pyridine compounds include 2-, 3-, and 4-(trichloromethyl)pyridine, 2-chloro-6-(trichloromethyl)pyridine, 2-chloro-5-(trichloromethyl)pyridine, 2-chloro-4-(trichloromethyl)pyridine, 3-chloro-5-(trichloromethyl)pyridine, 2,6-dichloro-3-(trichloromethyl)pyridine, 2,6-dichloro-4-(trichloro-m 3,6-dichloro-2-(trichloromethyl)pyridine, 2,3-dichloro-5-

(trichloromethyl)pyridine, 2,3,6-trichloro-5-(trichloromethyl)pyridine, 2,3,5-trichloro-6-(trichloromethyl)pyridine, 2,3,5-trichloro-4-(trichloromethyl)pyridine, 2,3,4,5-tetrachloro-6-(trichloromethyl)pyridine, and 2,3,5,6-tetrachloro-4-(trichloromethyl)pyridine. Mixtures of (trichloromethyl)pyridines of Formula I may be employed. These compounds and their preparation are known in the art.

The (trichloromethyl)pyridine compounds of Formula II are typically employed in the process of the present invention as a solution in an inert solvent. Chlorocarbon solvents, such as tetrachloroethylene, methylene chloride, and chlorobenzene, and hydrocarbon solvents, such as toluene, xylene, and hexane, are typical. Tetrachloroethylene is sometimes preferred. Solutions containing from about 5 to about 80 percent compound of Formula 11 are often employed.

Aluminum oxide (alumina) comes in a variety of forms, all of which have some utility in the present invention. Gamma-alumina is preferred. The catalyst is typically employed in an amount of from about 0.1 to about 200 percent of the weight of the compound of Formula II employed. Further, a sufficient amount of the catalyst is typically employed so that the contact time between the reactants and the catalyst in a vapor phase reactor will be about 0.1 to about 50 seconds.

To carry out the process to obtain a pyridinecarboxylic acid chloride of Formula 1, alumina is placed in a vapor phase reactor and heated to the desired temperature and then a (trichloromethyl)pyridine compound of Formula 11, optionally dissolved in an inert solvent, is vaporized and passed through the reactor. The vapor is typically subsequently condensed by cooling or by absorption into a miscible liquid to recover the desired product.

The process is usually carried out at a temperature of between about 250° C. and about 450° C. Temperatures between about 300° C. and about 400° C. are preferred. At temperatures that are too low, the products are not readily desorbed from the catalyst and at temperatures that are too high, decomposition of the reactants and products takes place. The pressure in the reactor is not important except for its effect on the boiling points of the substrate and the product of the process At pressures that are too high, it is not possible to vaporize the starting material at a suitable temperature and at pressures that are too low, it is difficult to condense the products.

To carry out the process to obtain a pyridinecarboxylic acid, ester, or amide compound of Formula III, a pyridinecarboxylic acid chloride compound of Formula I is prepared as described above and then the compound prepared is contacted with water, an aliphatic alcohol of 1-12 carbon atoms, ammonia, or a primary or secondary alkylamine having 1-12 carbon atoms in each alkyl moiety. The water may contain a base or acid catalyst to assist the hydrolysis. Suitable aliphatic alcohols include methanol, ethanol, butanol, 1-methylethanol (isopropyl alcohol), 1,1-dimethylethanol (tertiary butyl alcohol), decanol, 1-methylheptanol, 2-methylpropanol, and the like. Suitable primary and secondary alkylamines include methylamine, hexylamine, 2,3-dimethyldecylamine, 1-methylbutylamine, diethylamine, N-methyloctylamine, bis(1-methylpropyl)amine, and the like.

The reaction can be carried out under a wide variety of conditions as is known in the art. It is convenient to conduct it at ambient temperatures, typically, between about 0° C. and 100° C. Generally, the pyridinecarboxylic acid chloride of Formula I is added to an excess of the water, alcohol, ammonia, or amine and the mixture is allowed to react. An inert solvent may be employed. In the case of reaction with water, a solvent that dissolves both water and the compound of Formula I is generally helpful. Such solvents include acetonitrile, acetone, and the like. In the case of alcohols, a large enough excess of the alcohol to act as a solvent is typically employed. In the case of ammonia, water is a convenient solvent since ammonia reacts much faster than water, and in the case of amines, inert solvents such as methylene chloride, tetrachloroethylene, toluene, and hexane are often employed. The pyridinecarboxylic acid derivative products of Formula III can be recovered by conventional means.

EXAMPLES

Example 1

Preparation of Dichloronicotinoyl Chloride and Methyl 2,6-Dichloronicotinoate

A 22 mm diameter by 28 inches (11 cm) length quartz tube packed in the center with 15.0 g of Harshaw Al-3945 E1/16 gamma-alumina and on the top with Pyrex TM beads (to facilitate vaporization of materials added to the tube) surrounded by a ceramic fiber heater and having an external thermocouple was employed. The tube had an inlet at the top and an exit at the bottom that was connected to a cold trap. The tube was heated to 350° C. and a 6.1 weight percent solution (containing 19.1 g) of 2,6-dichloro-3-(trichloromethyl)pyridine in tetrachlorethylene was pumped through the heated tube at the rate of 2.02 g/min. The retention time was calculated to be 1.0 sec. Dichloronicotinoyl chloride collected in the cold trap. A large excess of methanol was added to the cold trap and all of the exit lines were flushed with methanol and the flushate added to the cold trap. The contents of the cold trap were subsequently analyzed by gas chromatography using an internal standard and the only organic product found to be present was methyl 2,6-dichloronicotinoate. The conversion was 100 percent and the yield was 70 percent of theory.

Example 2

Preparation of 3,6-Dichloropicolinoyl Chloride and Methyl 3,6-Dichloropicolinate The reactor of Example 1 loaded with 15.0 g of the same gamma-alumina was heated to 356° C. and a 7.2 weight percent solution in tetrachloroethylene (containing 18.5 g) of 3,6-dichloro-2-(trichloromethyl)pyridine was pumped in at the rate of 2.03 g/min over a 127 min. period. The retention time was calculated to be 1.0 sec. Methanol then was added to the 3,5-dichloropicolinoyl chloride that was collected cold trap and the resulting mixture was subsequently analyzed by standardized gas chromatography and found to contain methyl 3,6-dichloropicolinate in 9.6 percent yield and 2,5-dichloropyridine in 10.4 percent yield. The overall recovery was 37 percent.

Example 3

Preparation of a Mixture of Methyl Picolinates

The reactor of Example 1 loaded with 15.0 g of the same gamma-alumina was heated to 313° C. and a 5.2 weight percent solution of an equimolar mixture of 2,3-dichloro-5-(trichloromethyl)pyridine, 2,6-dichloro-3-(trichloromethyl)pyridine, 2,3-dichloro-6-(trichlo methyl)pyridine in tetrachloroethylene was fed to the reactor at the rate of 1.56 g/min over a 110 min period. The effluent that collected in the cold trap was diluted with methanol and the mixture was subsequently analyzed by standardized gas chromatography to contain the following:

2,6-dichloro-3-(trichloromethyl)pyridine: 12.7 mole %:
methyl 2,6-dichloronicotinate: 30.0 mole %:
2,3-dichloro-5-(trichloromethyl)pyridine: 19.4 mole %:
methyl 2,3-dichloronicotinate: 22.8 mole %:
2,3-dichloro-6-(trichloromethyl)pyridine: 10.2 mole %:
unknown: 4.9 mole %.

Example 4

Preparation of 2,6-Dichloroisonicotinoyl Chloride and Methyl 2,6-Dichloroisonicotinate The reactor of Example 1 loaded with 15.0 g of the same gamma-alumina was heated to 365° C. and a 5.4 weight percent solution of 2,6-dichloro-4-(trichloromethyl)pyridine in tetrachloroethylene was fed to the reactor at the rate of 1.91 g/min over a 150 min period. The calculated retention time was 0.8 sec. The effluent that collected in the cold trap was diluted with methanol and after a short time the mixture was analyzed by standardized gas chromatography to contain 56.5 percent of the theoretical amount of methyl 2,6-dichloroisonicotinate as a mixture with unreacted starting material. The molar recovery was 70 percent.

What is claimed is:

1. A process for the preparation of a pyridinecarboxylic acid chloride compound of the formula

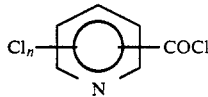

wherein n represents an integer of 0 to 4
which comprises contacting a (trichloromethyl)pyridine compound of the formula

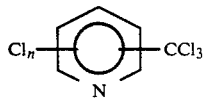

wherein n represents an integer of 0 to 4
in the vapor phase with aluminum oxide at a temperature of about 250° C. to about 450° C.

2. A process according to claim 1 wherein the aluminum oxide is gamma-alumina.

3. A process according to claim 1 wherein the (trichloromethyl)pyridine compound is put into the vapor phase by vaporizing a solution thereof in an inert solvent.

4. A process for the preparation of a pyridinecarboxylic acid or ester or amide derivative thereof of the formula

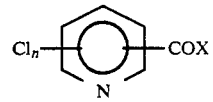

wherein

X represents OH, O($C_1$–$C_{12}$ alkyl), $NH_2$, NH($C_1$–$C_{12}$ alkyl), or N($C_1$–$C_{12}$ alkyl)$_2$; and n represents an integer of 0 to 4
which comprises contacting a (trichloromethyl)pyridine compound of the formula

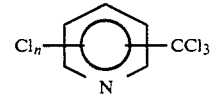

wherein n represents an integer of 0 to 4
in the vapor phase with aluminum oxide at a temperature of about 250° C. to about 450° C. to obtain a pyridinecarboxylic acid chloride compound of the formula

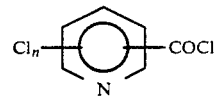

wherein n represents an integer of 0 to 4
and subsequently combining said acid chloride compound with water, an aliphatic alcohol having 1 to 12 carbon atoms, ammonia, or a primary or secondary alkylamine having 1 to 12 carbon atoms in each alkyl moiety.

5. A process according to claim 4 wherein the aluminum oxide is gamma-alumina.

6. A process according to claim 4 wherein the (trichloromethyl)pyridine compound is put into the vapor phase by vaporizing a solution thereof in an inert solvent.

7. A process according to claim 4 wherein the acid chloride compound is combined with methanol to obtain a methyl ester pyridinecarboxylic acid derivative.

* * * * *